(12) United States Patent  (10) Patent No.: US 9,146,188 B2
Yamasaki et al.  (45) Date of Patent: Sep. 29, 2015

(54) VARIABLE FLOW PATH WIDTH VIRTUAL IMPACTOR AND PARTICLE DETECTING DEVICE

(71) Applicant: Azbil Corporation, Tokyo (JP)

(72) Inventors: Shinsuke Yamasaki, Tokyo (JP); Hidekazu Takahashi, Tokyo (JP)

(73) Assignee: AZBIL CORPORATION, Tokyo (JP)

( * ) Notice: Subject to any disclaimer, the term of this patent is extended or adjusted under 35 U.S.C. 154(b) by 8 days.

(21) Appl. No.: 14/074,211

(22) Filed: Nov. 7, 2013

(65) Prior Publication Data

US 2014/0123730 A1 May 8, 2014

(30) Foreign Application Priority Data

Nov. 7, 2012 (JP) .................................. 2012-245823

(51) Int. Cl.
*G01N 15/00* (2006.01)
*G01N 15/06* (2006.01)
*G01N 15/02* (2006.01)
*B01D 45/04* (2006.01)

(52) U.S. Cl.
CPC ........ *G01N 15/0618* (2013.01); *G01N 15/0255* (2013.01); *B01D 45/04* (2013.01); *G01N 2015/0261* (2013.01)

(58) Field of Classification Search
CPC .................. G01N 15/0205; G01N 2015/0261
See application file for complete search history.

(56) References Cited

U.S. PATENT DOCUMENTS 5,006,227 A * 4/1991 Behm et al. .................. 73/28.01

FOREIGN PATENT DOCUMENTS

JP  2012-141277 A  7/2012
WO  2010/080643 A1  7/2010

OTHER PUBLICATIONS

Ding et al., Development of a High Volume Slit Nozzle Virtual Impactor to Concentrate Coarse Particles, Aerosol Science and Technology 34 (2001) pp. 274-283.

* cited by examiner

*Primary Examiner* — Laura Martin
*Assistant Examiner* — Alex Devito
(74) *Attorney, Agent, or Firm* — Troutman Sanders LLP

(57) ABSTRACT

A virtual impactor includes a jet nozzle that jets, from a jet outlet, a gas that contains particles, an opposing nozzle that is disposed with a specific separation distance from the jet nozzle and draws in, as a secondary flow, from a vacuum inlet at one end portion, a portion of the gas that is jetted from the jet nozzle, and a variable mechanism that varies at least one of a width of the jet outlet, the specific distance, and a width of the vacuum inlet.

1 Claim, 13 Drawing Sheets

FIG. 11

Airborne Particles

Exhaust

Exhaust

Condensed Particles

VARIABLE FLOW PATH WIDTH VIRTUAL IMPACTOR AND PARTICLE DETECTING DEVICE

CROSS REFERENCE TO RELATED APPLICATION

This application claims priority under 35 U.S.C. §119 to Japanese Patent Application No. 2012-245823, filed on Nov. 7, 2012, the entire content of which being hereby incorporated herein by reference.

FIELD OF TECHNOLOGY

The present invention relates to an improvement in a virtual impactor device that is used when condensing particles in a fluid or separating particles in a fluid by particle size, and relates to a particle detecting system (device) that uses the improved virtual impactor.

BACKGROUND

Detecting devices for detecting particles in the gases or in fluids are required in many situations, such as in manufacturing facilities for foodstuffs, pharmaceuticals, and general industrial products, in laboratories, in indoor environment measurements (testing for allergens), in monitoring atmospheric pollution microparticles, and the like. That which exists in the gas or liquid that is subject to detection by the detecting device includes not only microparticles as simple physical entities (for example, mite carcasses and feces, pollen, sulfides, and the like), but also includes bacteria, funguses (molds), mycoplasmas, and other microorganisms as well.

For example, when detecting atmospheric airborne microparticles or microorganisms, it is possible to collect samples using a filter and then to make observations either directly or after cultivation (for microorganisms), but doing so has drawbacks from the perspective of real-time processing. Given this, an optical particle detecting device has been developed wherein particles are illuminated with an inspection light, and scattered light or florescent light is detected. See, for example, International Patent Application Publication No. WO 2010/080643. An electric signal is outputted when a particle is detected, and thus this is well suited to real-time processing.

In order to increase the inspecting rate for the gas that is subject to analysis (or to increase the analysis efficiency for particles) in the particle detecting device set forth above, one may consider using means for collecting (condensing), into a relatively small volume of the gas flow, particles from a relatively large volume of the gas that is to be inspected. Condensing means can be produced through, for example, establishing a threshold value for a particle sorting device, for sorting particles by a specific particle diameter, between particles and gas molecules. The condensing means (or particle separating means) may be of an impactor method (and inertial impact type), a cyclone method (a centrifugal separating type), or a virtual impactor type, or the like.

For example, in the virtual impactor approach (a virtual inertial impact type), the impact plate in the impactor approach is removed, and instead an opposing nozzle is provided, where the large particles from among the particles that are accelerated by a jet nozzle are captured while passing through the opposing nozzle, to separate the microparticles (described below). An example of this type of condensing method is described in, for example, Yiming Ding et al., Development of a High Volume Slit Nozzle Virtual Impactor to Concentrate Coarse Particles, Aerosol Science and Technology, Mar. 1, 2001.

Moreover, for example, Japanese Unexamined Patent Application Publication No. 2012-141277 describes an example wherein flow rates (flow speeds) in a particle separating device (a cyclone or a virtual impactor) are set in multiple gradations, and a plurality of particle separating device outputs, with different particle selecting characteristics are selected, to specify the particles to be detected (microorganisms, allergens, or the like) depending on the sizes of the applicable particles, whether or not they fluoresce, and the like.

However, in a virtual impactor the particles that are well-suited to selection are determined by the physical specifications of the virtual impactor (the flow path width, the processing flow rate, and the like, of the virtual impactor). When a virtual impactor is used, the inertia that acts on the particles of specific diameters is determined through, for example, setting the gas flow speed (flow rate) of the gas that flows in the virtual impactor to a specific value, to set the separating conditions depending on the size of the particles, to condense the particles or separate the particles.

Because of this, in order to set (adjust) the virtual impactor to a specific vacuum pressure, a vacuum pump, having a specific flow rate specification, and a regulator (a pressure adjusting device) for setting/adjusting the gas flow rate are required separately from the virtual impactor. A regulator is relatively expensive, and produces pressure loss, and, to that extent, prevents the effective use of the vacuum pressure from the pump.

Moreover, even with a structure that is able to select the diameters of particles to be outputted by setting the gas flow rate to a specific value and providing a plurality of virtual impactors having different shapes (referencing, for example, FIG. 33 of Cited Document 2), still the number of virtual impactors is increased, increasing the cost.

Consequently, an aspect of the present invention is to provide a virtual impactor (a particle condensing device) and particle detecting device wherein the processing flow rate of the airflow that includes the particles that are to be condensed can be adjusted without the use of an external device, such as a pressure adjusting device.

Moreover, another aspect of the present invention is to provide a virtual impactor (particle separating device) and particle detecting device structured so as to enable the selection criterion for sorting by particle size to be varied, to eliminate the need for a plurality of particle separating devices.

SUMMARY

An example of the present invention provides a virtual impactor including a jet nozzle that jets, from a jet outlet, a gas that contains particles, and an opposing nozzle that is disposed with a specific separation distance from the jet nozzle and draws in, as a secondary flow, from a vacuum inlet at one end portion, a portion of the gas that is jetted from the jet nozzle. The virtual impactor further includes a variable mechanism that varies at least one of a width of the jet outlet, the specific distance, and a width of the vacuum inlet.

The use of this structure enables a structure wherein, in the nozzle portion wherein the flow path of the virtual impactor is constricted, a parameter, such as the width of the nozzle opening (the cross-sectional area of the fluid) can be varied. Doing so makes it possible to vary the characteristics of the particle separation (or the particle condensation) in the gas (fluid) of the virtual impactor, and to adjust a flow rate of the gas.

Preferably, the virtual impactor further includes a secondary vacuum unit that exhausts, from the other end portion of the opposing nozzle, the secondary flow that is drawn into the opposing nozzle, and a primary vacuum unit that draws, as a primary flow, the rest of the gas, excluding the secondary flow, that is jetted from the jet nozzle.

As a result, the gas is accelerated by the nozzle to cause the particles within the gas to advance directly toward the opposing nozzle, due to inertia, to be drawn in by the opposing nozzle, to be included primarily in a second flow. On the other hand, the gas is drawn in by the nozzle portion to be exhausted as a primary flow. Particles can be separated depending on size through setting the inertia.

Preferably, the variable mechanism is actuated by an electric signal that is provided from the outside. Doing so enables automated adjustments to the flow path of the nozzle portion of the virtual impactor.

Preferably, the jet outlet and the vacuum inlet are formed in the shape of slits (long thin gaps). Doing so causes the structure of the adjusting mechanism for the flow path widths of the nozzle portion to be relatively simple. If the jet outlet and the vacuum inlet were circular, one could consider structuring identically to an iris mechanism of a camera lens, but this would be complicated. Of course, this is not excluded from the adjusting mechanism in the present invention.

Preferably, the virtual impactor further includes a first detecting unit that detects a gas flow rate or pressure of the secondary flow and a second detecting unit that detects a gas flow rate or pressure of the primary flow, and a controlling unit that adjusts at least one of the jet outlet width, the separation distance and the vacuum inlet width, depending on a difference between a value that is detected and a target value that has been set in advance. Doing so enables the flow rates of the secondary flow and the primary flow to be adjusted by the virtual impactor.

A particle detecting device according to the present invention includes an optical detecting unit that detects a particle in a gas that is provided as the secondary flow from the virtual impactor. The particles are condensed in the secondary gas, increasing the efficiency of particle detection. Conversely, the particles are separated by size in the gas in the secondary flow, enabling evaluations that discriminate by size when performing particle detection.

Preferably, the particle detecting device outputs, to the controlling unit, a number of particles or a size of particles in the gas of the secondary flow, detected by the optical detecting unit, and the suitability of the adjustment of the virtual impactor (the width of the jet outlet, the separation distance, and the width of the vacuum inlet) is evaluated by the controlling unit based on the output from the optical particle detecting unit. Doing so makes it possible to provide a particle detecting device able to evaluate whether or not the virtual impactor is adjusted properly and whether or not the adjusting mechanism is operating properly.

Moreover, another example of the present application provides a virtual impactor including a first flow path wherein a fluid that includes particles flows, a second flow path that has a part that intersects the first flow path, and branches a portion of the fluid. The virtual impactor further includes a flow path width adjusting unit that changes a width of a flow path at an intersecting portion between the first flow path and the second flow path, to set a cross-sectional area of the fluid to a desired value.

Structuring in this way enables adjustments in the cross-sectional areas of the individual flow paths in the virtual impactor, making it possible to set the gas flow rates to desired values, making it possible to eliminate the regulator for setting and adjusting the gas flows, and possible to eliminate the pressure loss in the regulator. This enables a reduction in device manufacturing cost and setup cost.

Preferably, a jet nozzle and an opposing nozzle are formed across the second flow path at the intersecting portion of the first flow path. Doing so causes functioning as a virtual impactor.

Preferably, in the virtual impactor set forth above, the flow path width adjusting unit includes four flow path structuring members disposed in the shape of a matrix, a top plate and a bottom plate with both faces of the four flow path mechanism members held therebetween, and a distance adjusting unit that adjusts a separation distance between flow path structural members. Doing so enables the widths of the flow paths at the intersecting portion between the first flow path and the second flow path to be varied, to set the fluid cross-sectional areas to desired values.

In the present invention, the virtual impactor (a particle concentrating device) includes movable side plates, having through holes for forming an inlet and an outlet of a first flow path or a second flow path, movable flow path structuring members for forming a sidewall of the first flow path or the second flow path, a top plate and a bottom plate that are secured with the side plates and the flow path forming members held therebetween, and a member for increasing or decreasing forcibly the distance between the top plate and the bottom plate.

This structure makes it possible to adjust the cross-sectional areas of the individual flow paths by the virtual impactor alone, making it easy to set the required values, thus enabling the provision of a simple device structure and enabling an improvement in the convenience of use of the device.

Moreover, the particle detecting device includes the virtual impactor (the particle concentrating device) set forth above, a particle detector that detects particles from a gas that includes airborne particles that are condensed by the impactor, a first pump that maintains, at a specific value, the flow rate (secondary flow) of a gas that includes the particles in the virtual impactor, and a second pump that maintains, at a specific value, the flow rate (primary flow) of the exhaust of the virtual impactor.

Structuring as set forth above enables the cross-sectional areas of the individual flow paths to be adjusted by the virtual impactor, making it possible to set to the required values, and stabilizes the gas flow rates, thus making it possible to eliminate the regulator. This enables a reduction in the manufacturing cost of the equipment as a whole, and a reduction in the setup cost.

Moreover, in the present invention the particle detecting device includes a unit that resets the cross-sectional area of the second flow path by a cross-sectional area of the fluid of the second flow path that is determined through performing a specific calculating process by referencing, for example, a specific characteristic graph, a calculating formula, or the like, or a database, or the like, based on a measured flow rate value of the exhaust of the virtual impactor.

Structuring as set forth above makes it possible to adjust the cross-sectional areas of the fluids in the individual flow paths in the virtual impactor nozzle portions, making it easy to set to the flow rates required by the desired fluids.

The virtual impactor according to the present invention enables the widths of the flow paths (the cross-sectional areas of the fluids) within the virtual impactor to be adjusted, making it possible to set the flow rates of the flow paths to the required values.

BRIEF DESCRIPTIONS OF THE DRAWINGS

FIG. 11 is an explanatory diagram for explaining the operating theory of the virtual impactor.

DETAILED DESCRIPTION

Examples according to the present invention will be explained below, referencing the drawings. While the examples according to the present invention are applied to an airborne particle detector for detecting and measuring airborne microorganism particles, this is no more than a simple illustration of an example according to the present invention, and does not limit the present invention. This may be applied also to a device for detecting particles in a liquid, for detecting and measuring, for example, microorganisms particles in a liquid.

Comparative Example

Figure 12:
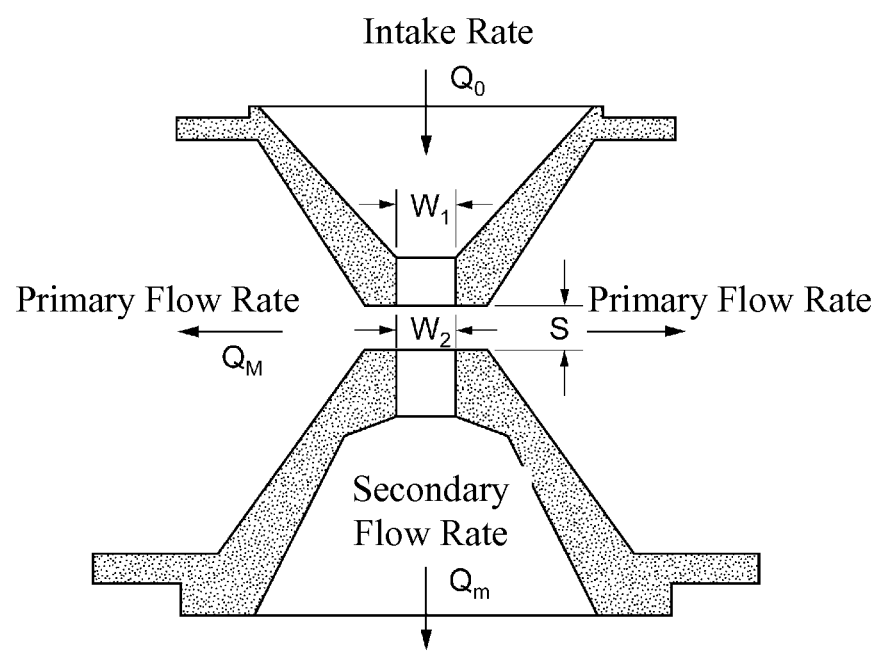
FIG. 12 is an explanatory diagram for explaining an example of the physical structure of the virtual impactor.

An ordinary virtual impactor will be explained first. FIG. 11 is an explanatory diagram illustrating the theory of a virtual impactor. FIG. 12 illustrates an ideal example structure of a virtual impactor.

In FIG. 11, the particles floating in the air includes particles such as microorganisms, and the like, that are subject to detection. In the center portion of the device, gas from the upper portion is drawn downward and accelerated by a jet nozzle wherein the diameter becomes smaller, where the inertia of the particles included in this gas causes the particles to travel straight downward. In a gap portion between the jet nozzle and the opposing nozzle, a gas is drawn in the horizontal direction and exhausted. The result is that, because the masses of the particles are greater than the masses of the gas molecules that carry the particles, inertia causes them to travel straight across the gap portion to be drawn in by the opposing nozzle. The gas molecules and the particles for which the difference in mass is small are drawn in the gap portion and move in the horizontal direction, to be exhausted. The result is that, of the gas that includes floating particles, that gas that passes through the exhaust gas in the sideways direction to arrive at the opposing nozzle will be in a state wherein the floating particles are condensed (condensed particles), and will be drawn downward.

As illustrated in FIG. 12, a portion of the gas of the inlet flow QO crosses the gap (with the width S) from the jet outlet (which has an opening diameter of W1) from the jet nozzle, to pass through the vacuum inlet (which has an opening diameter of W2) of the opposing nozzle, to be drawn into the opposing nozzle, to become the secondary flow Qm. This secondary flow Qm includes a large number of particles. The other portion of the gas in the inlet flow QO is drawn in the horizontal direction into the gap (with the width of S) to form the primary flow QM. The secondary flow Qm and the primary flow QM are drawn by pumps, not shown. The secondary flow rate Qm is set to be less than the primary flow rate QM, to cause the particles to be condensed in the secondary flow Qm. The secondary flow Qm is sent to the particle detector.

Figure 13:
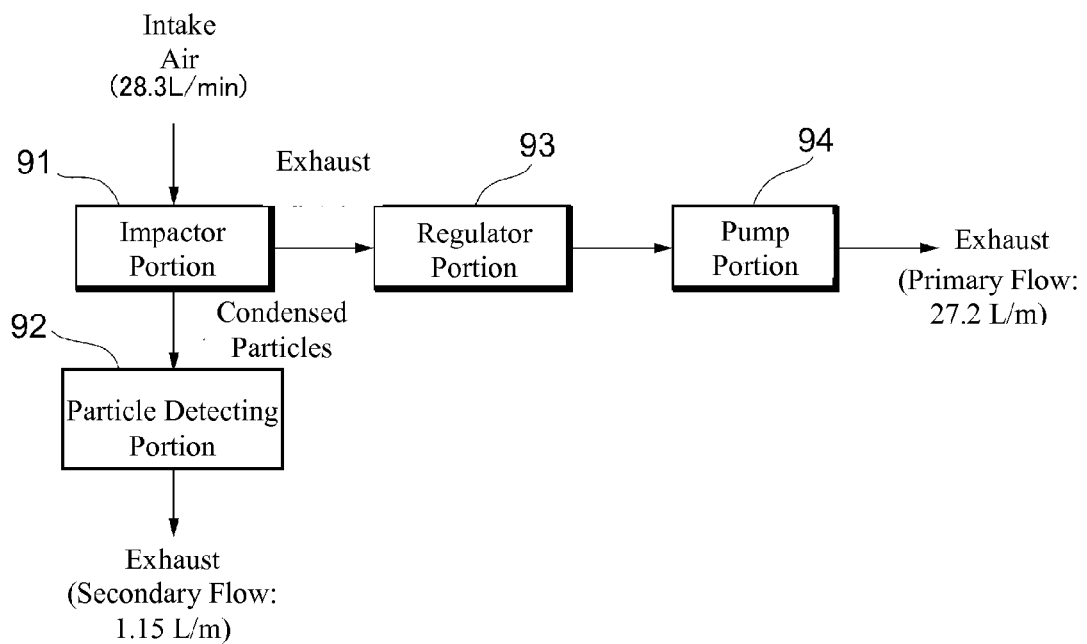
FIG. 13 is an explanatory diagram for explaining an example structure of a particle detecting device that uses a virtual impactor of a comparative example.

FIG. 13 is a block diagram for explaining an example structure of a particle detecting device that uses the virtual impactor according to the comparative example set forth above. The particle detecting device is structured from the virtual impactor (the particle condensing device) 91, a particle detecting portion 92, a regulator portion 93, and a pump portion 94. The particles in the gas are condensed by the virtual impactor 91, and supplied to a scattered light-type particle detecting portion 92, where the inorganic particles, microorganism particles, and the like, within the gas (the secondary flow) are detected. An air pump, not illustrated, is equipped within the particle detecting portion 92, to draw in the gas that is to be inspected, and to exhaust the gas to the outside after detection. The gas (primary flow) separated by the virtual impactor 91 is exhausted through the regulator 93, which adjusts the exhaust pressure, and through the air pump 94.

When structured in this way, if the gas that flows in is introduced at 28.3 L/min, for example, into the virtual impactor 91, a secondary gas that includes condensed particles will flow into the particle detecting portion 92 at a rate of 1.15 L/m, and a primary gas, from which the particles have been removed, will be exhausted at a rate of 27.2 L/min. As a result, the particle detecting portion 92 will perform particle detection corresponding to the intake air of 28.3 L/min on 1.15 L/min of gas, so the detection efficiency will be good.

Examples

In the structure of the comparative example, set forth above, a regulator for adjusting the flow rate that flows to other than the air pump is used to cause the amount of air that is drawn from the virtual impactor portion 91 to be a constant amount (referencing FIG. 13). In the present example, the virtual impactor portion 91 is given the function of the regulator 93, eliminating the need for the regulator portion 93.

The virtual impactor (particle condensing device) according to the present invention has a variable width mechanism able to adjust appropriately the width W1 of the flow path to which the gas that includes the floating particles that have been sampled flows, the width S of the flow path through which the gas that does not include particles (wherein the number of particles is low) is exhausted, and the width W2 of the flow path through which the gas that includes particles (that includes a large number of particles) is exhausted, thereby enabling the processing flow rates to be adjusted. More specifically, the minimum width portions of each of the individual flow paths (for example, nozzle parts) can be adjusted through changing the positions of structural parts that structure the flow paths.

Note that the virtual impactor according to the present invention can be used also when separating particles by size. In this case, the widths of the respective flow paths are changed through changing the positions of structural parts that structure the individual flow paths for the flow path through which flows the gas that includes the particles that are to be sorted into a first size and the flow path through which flows the gas that includes particles that are to be sorted into a second size.

Example

Figure 1:
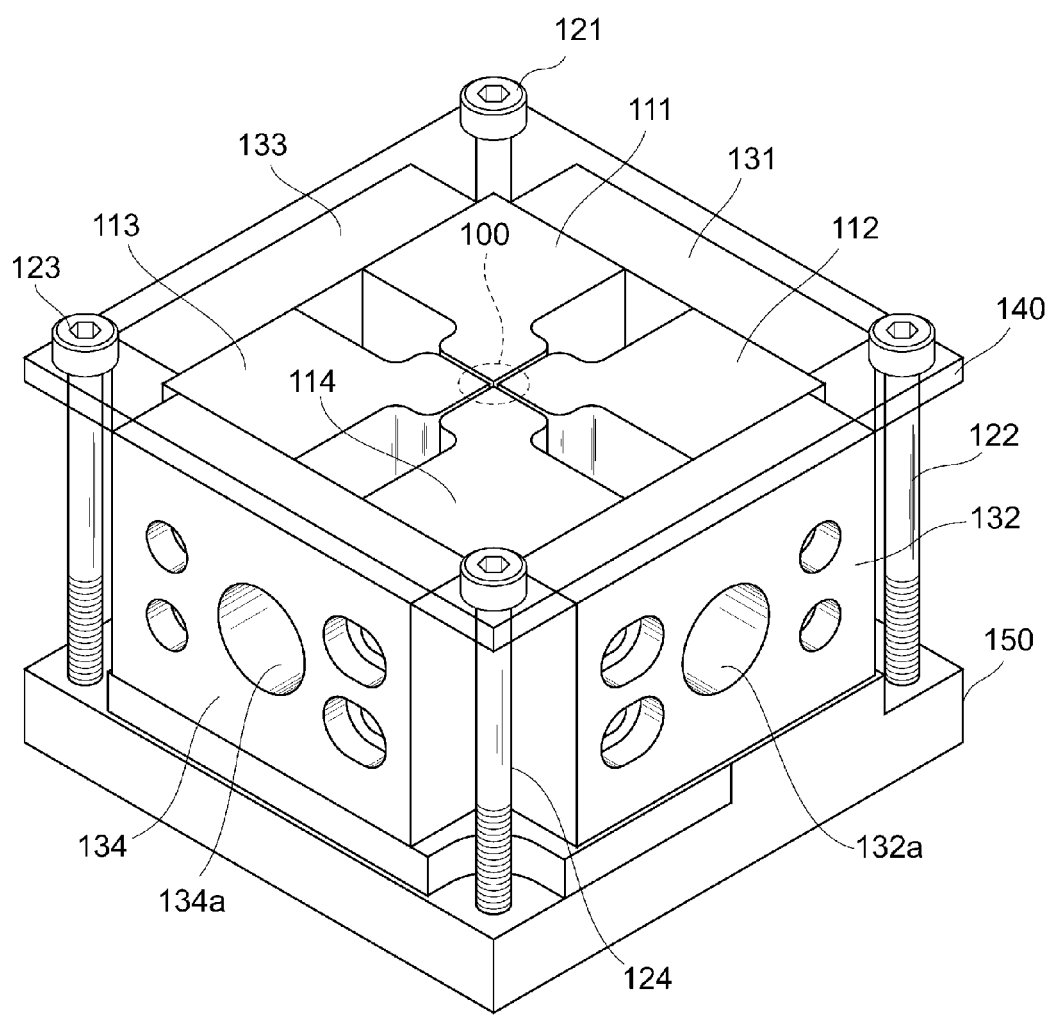
FIG. 1 is a perspective diagram for explaining an example of a variable flow path width virtual impactor according to the present invention.

FIG. 1 is a perspective diagram for explaining the externally visible structure of a variable flow path width virtual impactor according to Example according to the present invention. In this example, the structure enables the flow path widths to be adjusted by a manual operation. Note that for convenience in the drawings, the top plate 140 is shown as transparent, to enable the interior to be seen.

The virtual impactor (particle condensing device) illustrated in this figure includes, essentially, four flow path structuring members 111 through 114, four screws 121 through 124, four side plates 131 through 134, a top plate 140, and a bottom plate 150. The four flow path structuring members 111 through 114 are disposed in a 2×2 matrix, where the part in the center portion wherein the corner portions of the four members come together forms a flow path intersecting portion 100. The first flow path and the second flow path intersect at the intersecting portion 100. For example, the first flow path through which flows the gas that includes the sampled floating particles (the microparticles to be detected) is established from the upper right to the lower left in the figure. The inlet of the first flow path is the through hole 131*a* of the side plate 131, and the outlet is the through hole 134*a* of the side plate 134. Moreover, the second flow path, for exhausting (sucking out) a portion of the gas that flows in the first flow path, and which intersects the first flow path, is provided from the upper left to the lower right in the figure. One exhaust opening of the second flow path is the through hole 132*a* of the side plate 132. Moreover, the other exhaust opening of the second flow path is the through hole 133*a* of the side plate 133.

In the intersecting portion 100, the flow paths are narrowed through the flow path structuring members 111 through 114 being placed in mutual proximity, where the flow paths are wider at a location that is away from the intersecting portion 100. The parts wherein the flow paths are narrow (the gap portions) function as so-called nozzles. For example, the gap portion structured from the flow path structuring members 111 and 112 corresponds to a jet nozzle. The gap portion structured from the flow path structuring members 113 and 114 corresponds to the opposing nozzle. The gap portions structured from the flow path structuring members 111 and 112 and the flow path structuring members 113 and 114 correspond to the gap between the jet nozzle and the opposing nozzle (the separation distance).

The virtual impactor 1 illustrated in FIG. 1 has outer dimensions that are essentially a rectangular prism. Of course, there is no limitation to this shape. Through holes for connecting the respective gas flow paths are formed in each of the side plates 131 through 134 that surround the periphery of the four flow path structuring members 111 through 114. The four flow path structuring members 111 through 114 form the side walls of the first and second flow paths, and the individual flow path widths are set by the distances between the flow path structuring members, which can be operated and adjusted manually. When the layout positions of the individual flow path structuring members 111 through 114 have been determined, then the flow path structuring members 111 through 114 are secured through screws (not shown) to the side plates at the screw hole parts shown in the side plates 131 through 134. A top plate 140 and a bottom plate 150 are attached to the assembled flow path structuring members 111 through 114 and side plates 131 through 134. Note that a portion of the bottom plate 150 is structured so as to enable sliding, to facilitate convenience in adjustments.

The adjustment of the flow path widths after assembly of the virtual impactor 1 is performed through, for example, loosening the four screws 121 through 124 that secure the top plate 140 and the bottom plate 150, illustrated in FIG. 1, to the flow path structuring members 111 through 114, loosening the screws that secure, to the side plate, the flow path structuring member that is to be adjusted, and then adjusting the flow path width. The various screws are tightened after the adjustment. In this way, the user is able to achieve the specific flow path widths that are required, by setting and adjusting the widths of the individual flow paths (the cross-sectional areas of the fluids) in the intersecting portion 100 by making fine adjustments to the positions of the flow path structuring members manually.

Note that when performing the adjustments manually the adjustments can be achieved easily through the use of a shim gauge and appropriate tools to set the gap, but the adjustment can be performed more easily through a structure that enables the gap to be varied mechanically (such as a cam mechanism or a mechanism to move the member inward or outward using a screw), as in an example described below.

Figure 2:
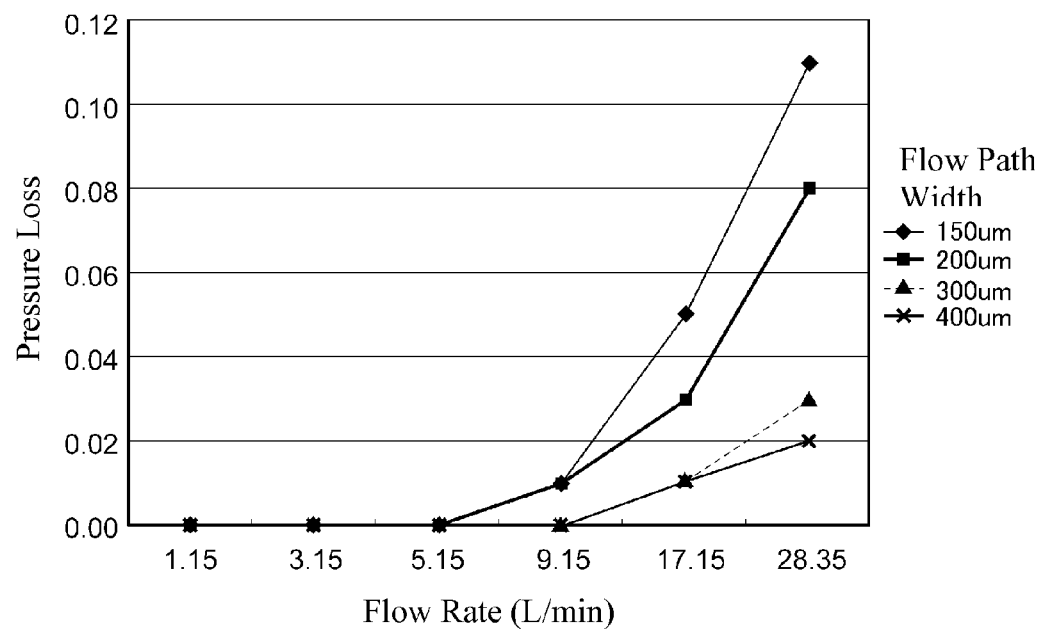
FIG. 2 is a graph illustrating an example of the flow path width versus pressure loss characteristics in the virtual impactor.

FIG. 2 is an example wherein the flow rate versus pressure loss characteristics for the primary flow of the virtual impactor 1 was measured for multiple different (primary flow) flow path widths S. The flow rate of the secondary flow is a flow rate that is sufficiently small when compared to the flow rate of the primary flow so as to be unaffected (referencing the flow rate in the reference example in FIG. 13). In FIG. 2, the graph with the diamond-shaped sampling points is an example wherein the flow path width S is set to 150 μm, the graph with the square sampling points is an example wherein the flow path width S is set to 200 μm, the graph with the triangular sampling points is an example wherein the flow path width S is set to 300 μm, and the graph with the X-mark sampling points is an example wherein the flow path width S is set to 400 μm. Note that the parts wherein the sampling points overlap are displayed at the sampling points wherein the flow path is wide. Basically, the following can be understood from these graphs. When the flow rate is low, at no more than 5 L/min, as in the reference example (corresponding to, for example, the flow rate of the secondary flow), there is no pressure loss regardless of the flow path width. When the flow rate is in excess of 9 L/min, pressure loss begins to be produced when the width of the flow path is narrower than 400 μm. Moreover, in a range wherein the flow rate is about 27 L/m, where the flow rate corresponds to the primary flow, a pressure loss corresponding to the reduction in the flow path width S of the primary flow is produced. Consequently, it can be seen that it is possible to adjust/set the flow rate of the primary flow through changing the flow path width of the primary flow through adjusting the positions of the flow path structuring members of the virtual impactor 1.

As described above, the structure of the virtual impactor 1 is a structure wherein an intersecting portion 100 that corresponds to the gap portion between the nozzles of the virtual impactor (referencing FIG. 12) is an intersecting portion of the two flow paths for the primary flow and the secondary flow, and thus functions as a jet nozzle and an opposing nozzle for the virtual impactor, for the secondary flow (the low-volume flow), and functions as a constriction of the flow path (a limitation on the flow path width) for the primary flow (the high-volume flow). Because of this, the virtual impactor 1 can function as a regulator for the primary flow over a given flow rate range, thereby making it possible to eliminate the regulator portions 93, described above. The virtual impactor 1 according to the present example, unlike the conventional virtual impactor, has a structure wherein the flow path width is variable, and can be adjusted by a user.

Another Example

Figure 3:
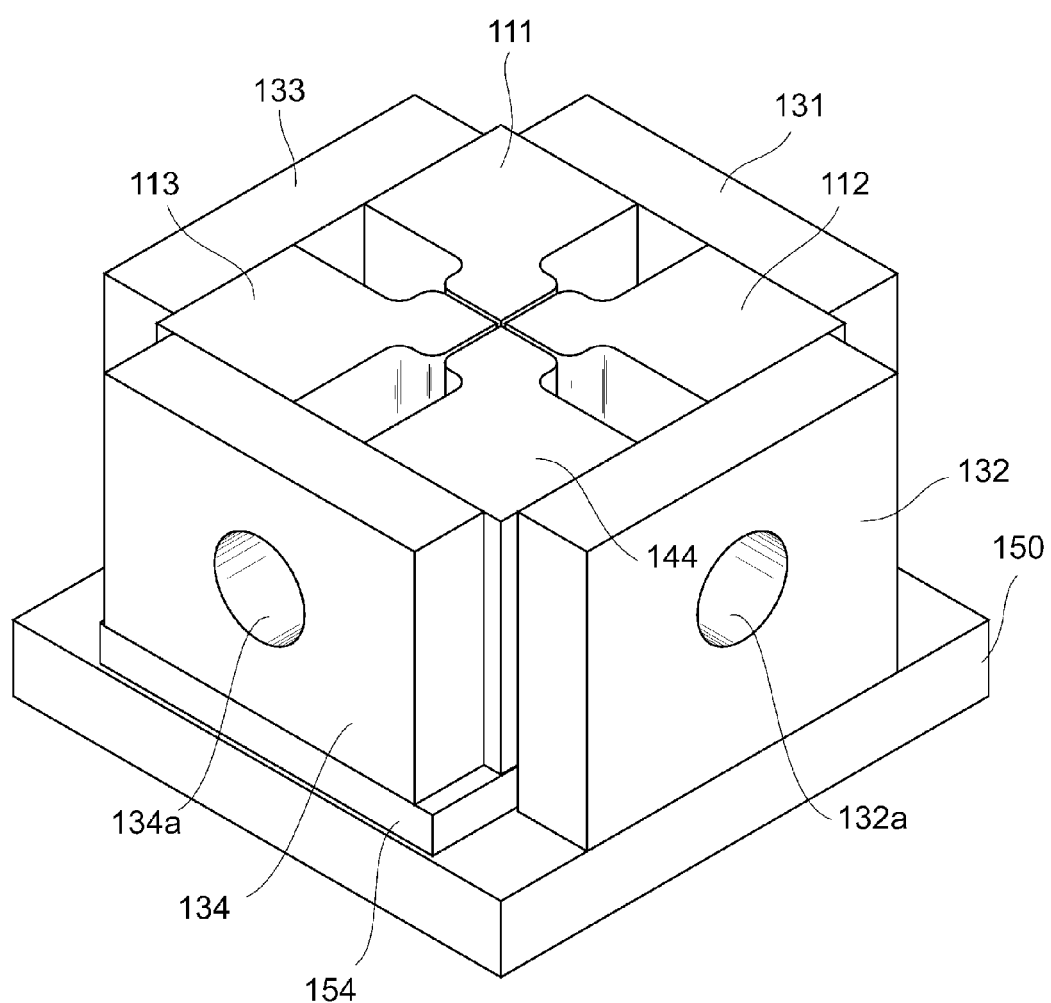
FIG. 3 is a perspective diagram for explaining another example of a variable flow path width virtual impactor.

FIG. 3 is a perspective diagram illustrating Another Example of a virtual impactor wherein the flow path width can be adjusted automatically. In this figure, parts corresponding to FIG. 1 are assigned identical codes, and explanations of these parts are omitted. In the example illustrated in FIG. 3, the state wherein the top plate 140 has been removed from the virtual impactor 1 has been removed is shown.

In the present example, the moving mechanisms for the flow path structuring members 111 through 114 are provided within the side plates 131, 132, and 134. The moving mechanisms correspond to actuators in the controlling device.

Figure 4:
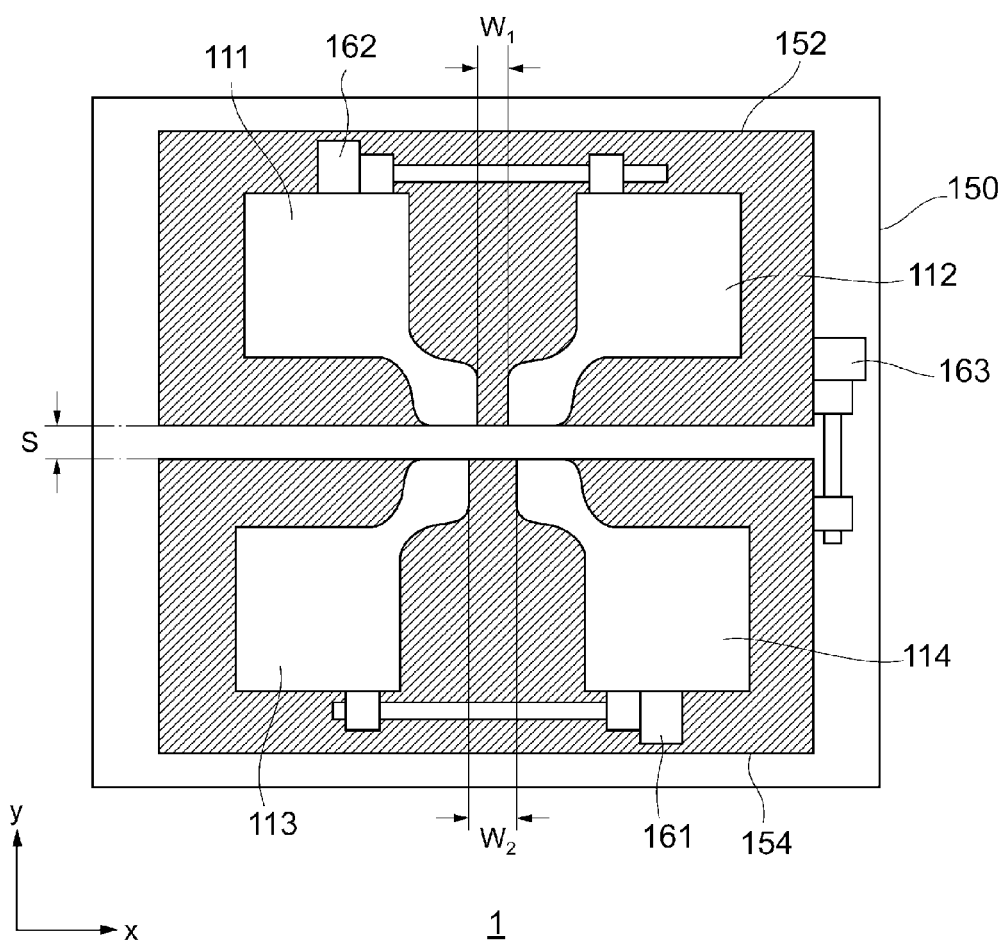
FIG. 4 is an explanatory diagram for explaining an example of a flow path varying mechanism for a variable flow path width virtual impactor.

FIG. 4 is an explanatory diagram for explaining the critical portions of the moving mechanisms, showing the state wherein the virtual impactor of FIG. 3 is viewed from above. A first subframe 152 is disposed secured to a region on the top half over the bottom plate 150 that is the base frame for the virtual impactor 1, and a second subframe 154 is disposed so as to be able to move in the up-down direction (the y direction in the figure) in the region of the bottom half. The movement of the subframe 154 is performed along with a sliding path (not shown) on the bottom plate 150. The flow path structuring member 111 is disposed in the region of the left side of the first subframe 152, and the flow path structuring member 112 is disposed in the region on the right side. For example, the flow path structuring member 111 is secured to the subframe 152, and the flow path structuring member 112 is attached so as to be able to move in the left-right direction (the x direction in the figure) along a sliding path (not shown) on the subframe 152. The flow path structuring member 113 is disposed in the region on the left side of the second subframe 154, and the flow path structuring member 114 is disposed in the region on the right side. For example, the flow path structuring member 113 and the flow path structuring member 114 are attached so as to be able to move in the left-right direction (the x direction in the figure) along a sliding path (not shown) on the subframe 154.

A moving mechanism 161 is connected between the flow path structuring member 113 and the flow path structuring member 114, and acts to move the flow path structuring member 113 and the flow path structuring member 114 together or apart. A moving mechanism 162 is connected between the flow path structuring member 111 and the flow path structuring member 112, and acts to move the flow path structuring member 112 toward or away from the flow path structuring member 111. Moreover, the first subframe 152 and the second subframe 154 are connected together by a moving mechanism 163. The subframe 152 and the subframe 154 are moved together or apart by the action of the moving mechanism 163. The moving mechanisms 161 through 163 are structured from motors, potentiometers, feed screws, frame securing nuts, and the like, where the degree of rotation of the motor is controlled by an electric signal that is supplied from the outside, and the amount of movement of the subframe 154 or of the flow path structuring members 112 through 114 are adjusted/set thereby. For an actuator (a moving mechanism) for fine adjustments, a piezoelectric material that produces morphological deformation and dislocation corresponding to the applied voltage, or a hydraulic (fluid) motor, a cylinder, or the like, may be used.

As illustrated in FIG. 4, the flow path width S for the primary flow (or the gap S between the subframes 152 and 154), set between the flow path structuring members 111 and 112 and the flow path structuring members 113 and 114, is set through operation of the moving mechanism 163. Moreover, the width W1 of the gas supply path that is set between the flow path structuring members 111 and 112 is adjusted/set by the moving mechanism 162. The width W2 of the gas supply path of the secondary flow between the flow path structuring members 113 and 114 is set by the moving mechanism 163.

Yet Another Example

Figure 5:
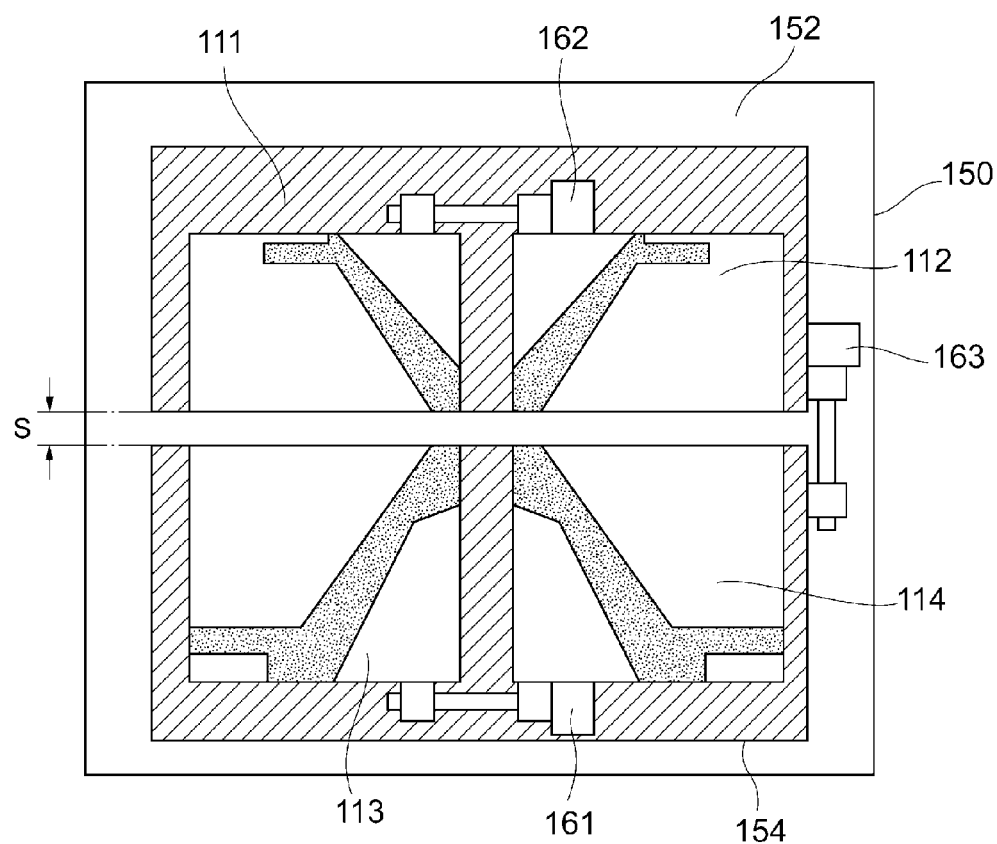
FIG. 5 is an explanatory diagram for explaining an example of another flow path varying mechanism for a variable flow path width virtual impactor.

FIG. 5 illustrates Yet Another Example. In this figure, parts corresponding to FIG. 4 are assigned identical codes, and explanations of these parts are omitted.

In this example, flow path structuring members 111 through 114 shaped similarly to the cross-section of a nozzle such as illustrated in FIG. 12, are attached to a base plate, where a moving mechanism is connected to part of the base plate. The widths of the flow paths can be adjusted with this structure as well.

Further Example

Figure 6:
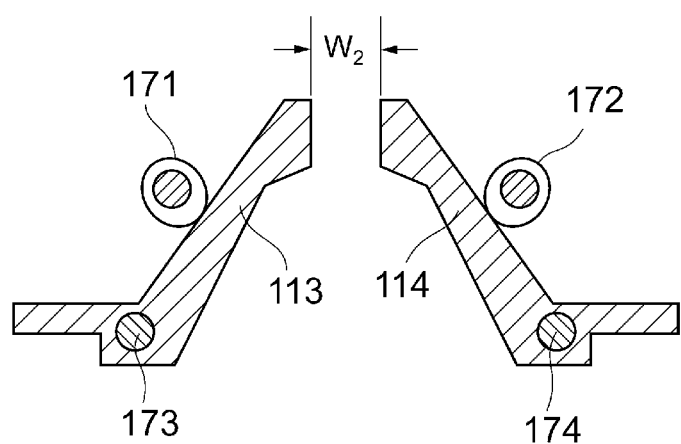
FIG. 6 is an explanatory diagram for explaining an example of another flow path varying mechanism for a variable flow path width virtual impactor.

FIG. 6 illustrates Further Example. In this example, the mechanism is one wherein the flow path structuring members 113 and 114 are swiveled around support points 173 and 175 by cam mechanisms 171 and 172 that are rotationally angularly driven by a motor, not shown, to adjust/set the flow path width between the flow path structuring members 113 and 114.

In this way, it is possible to adjust the width of the flow path of the primary flow and the width of the flow path of the secondary flow of the virtual impactor. The flow rate of the primary flow can be adjusted by adjusting the width of the flow path of the primary flow. Moreover, the sizes of the particles of the branch flow and the sizes of the particles subject to condensation can be adjusted through adjusting the width of the flow path for the secondary flow.

Another Further Example

Figure 7:
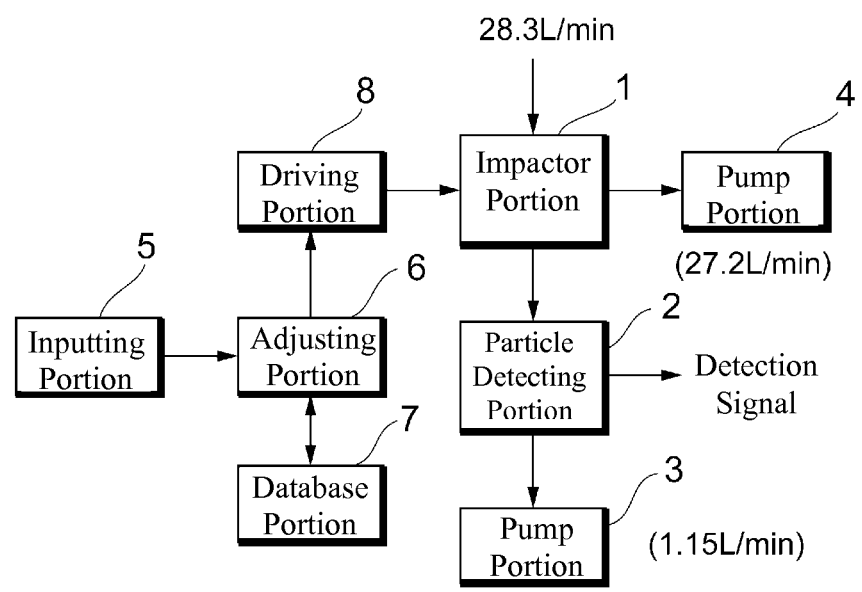
FIG. 7 is an explanatory diagram for explaining an example of feed-forward control of flow path widths in a variable flow path width virtual impactor according to the present invention.

FIG. 7 is an explanatory diagram for explaining an example of a particle detecting device that is provided with a variable flow path width virtual impactor as described above. In this example, the flow path width of the virtual impactor is adjusted through the so-called feed-forward approach.

In this figure, the particle detecting device is structured from the virtual impactor portion (the particle condensing device) 1 described above, a particle detecting portion 2, an air pump 3 (a first pump for drawing the secondary flow), an air pump 4 (a second pump for drawing the primary flow), an inputting portion 5, an adjusting portion (a computer system) 6, a database portion 7, a driving portion 8, and the like. The particle detecting portion 2 is, for example, a particle detector that uses the scattered light/florescent light detecting approach, described already in, for example, WO 2010/080643, to detect microparticles and microorganisms in real time. The database portion 7 has values for the parameters for the various portions, by which to achieve the specific operating conditions (for example, the gradations of particles, condensation of particles, etc.) stored in advance.

Figure 9:
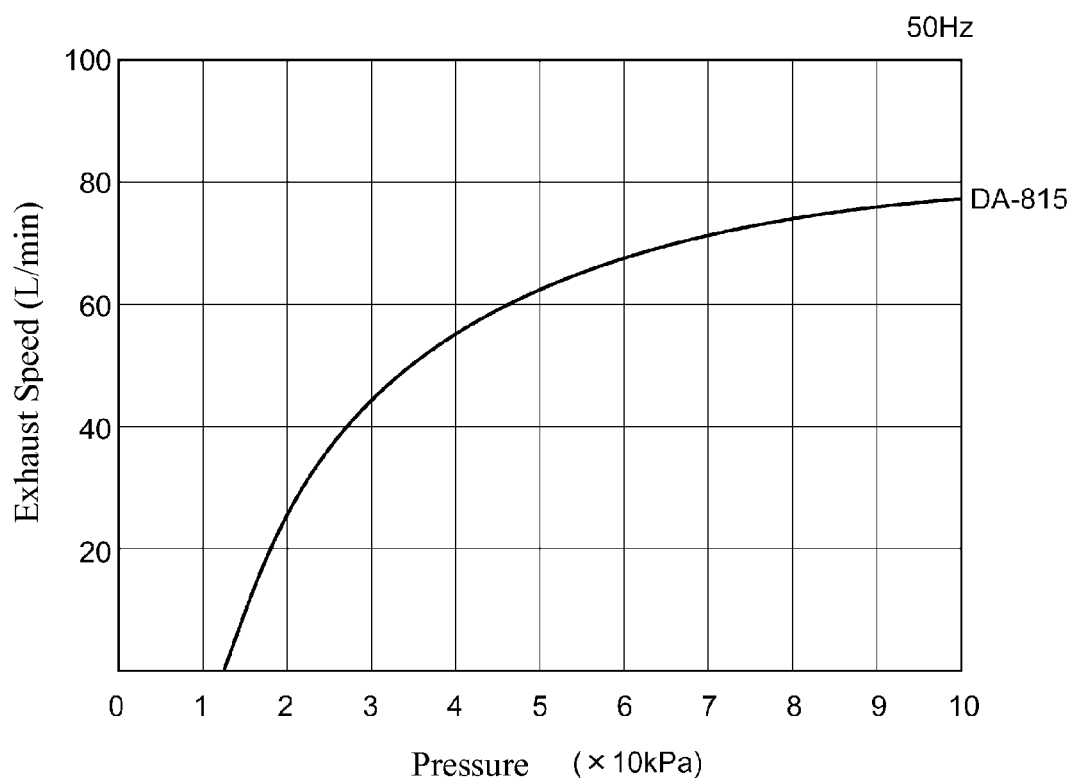
FIG. 9 is a graph for explaining an example of data illustrating the relationship between the air pump vacuum pressure and the exhaust flow rate, stored in the database portion.

The database portion 7, as illustrated in FIG. 9, stores, for example, the relationships between the suction pressure [kPa] of the air pumps for each of the pump portions and the exhaust flow rates (exhaust speeds) [L/min], where the exhaust flow rate in the pump unit is set when a specific vacuum pressure value is set by the electric power that is supplied to the pump motor (not shown). This makes it possible to set a rough value for the flow rate for the primary flow in the virtual impactor 1 through the pump portion 4. Furthermore, the flow rate QM of the primary flow can be adjusted through adjusting the flow path width S of the virtual impactor 1. Similarly, the flow rate of the secondary flow in the virtual impactor 1 can be set by the pump portion 3. Usually the flow rate Qm of the secondary flow is set to, for example, no more than $1/10$ of the total inflow QO (=QM+Qm) (although not limited thereto). When the total flow rate is large, the impact of the flow rate of the secondary flow on the flow rate of the primary flow is relatively small.

Figure 10:
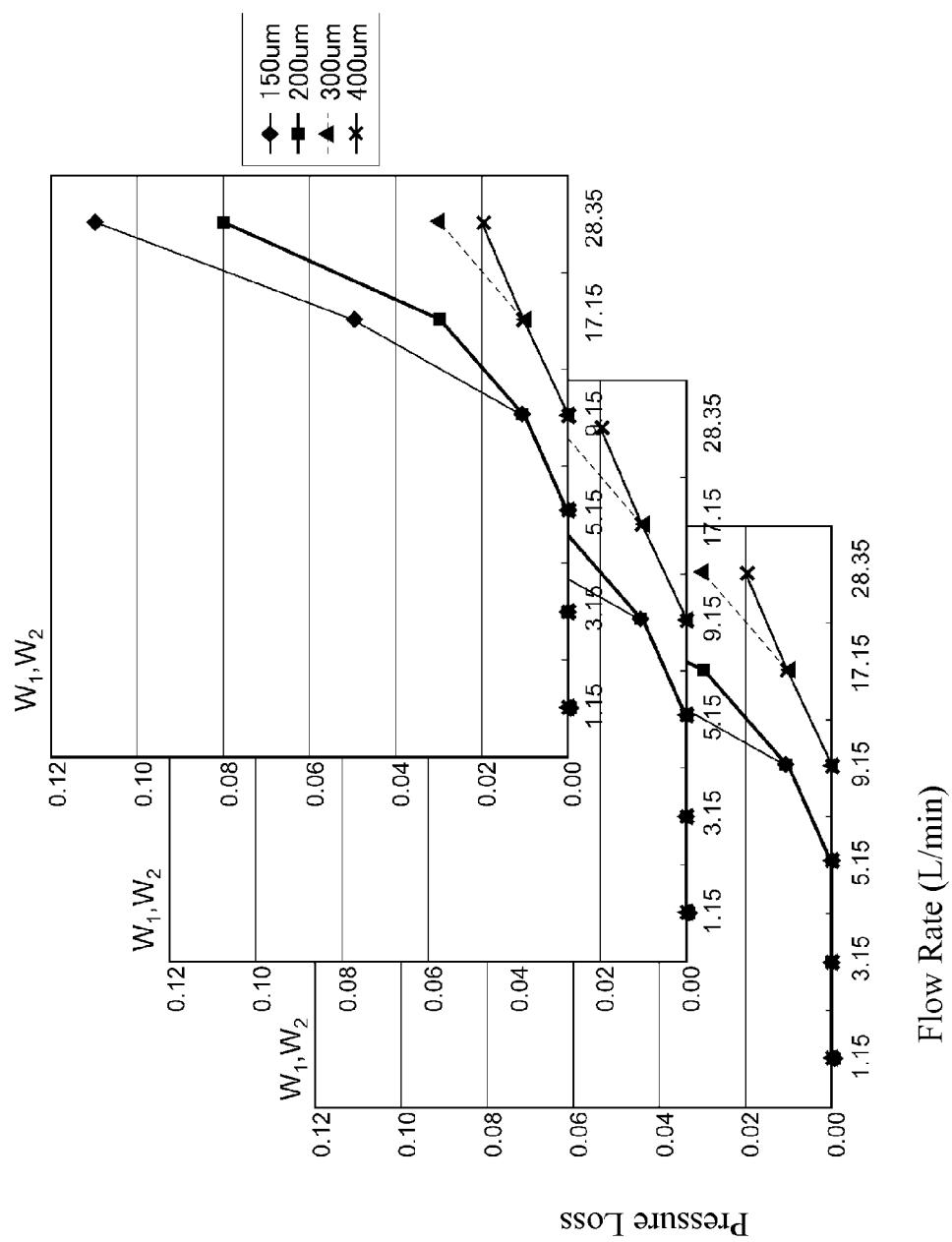
FIG. 10 is an explanatory diagram for explaining the relationship between flow rates and the pressure losses, shown as a graph, in setting up a plurality of parameters that are stored in the database portion.

Moreover, the database portion 7, as illustrated in FIG. 10, stores a large number of flow rate-versus-pressure loss characteristics when the flow path width S is set to multiple different values under multiple different conditions for the flow path widths W1 and W2 in the virtual impactor 1. This makes it possible to adjust/set the flow rate for the primary flow and the flow rate for the secondary flow more accurately through referencing such data.

The user sets the operating conditions through the inputting portion 5 that includes a keyboard, and the like. The adjusting portion 6 references the control parameter information for the various portions, stored in the database portion 7, corresponding to the operating conditions that have been specified, to drive the driving portion 8, to operate the actuators (motors, or the like) of the moving mechanisms 161 through 163 within the virtual impactor 1 portion, to set the widths of the first flow path (W1 and W2) and the width of the second flow path (S) of the virtual impactor portion 1 depending on the operating conditions. Moreover, the air pump 3 and the air pump 4 are operated to set the flow rates of the secondary flow and of the primary flow of the virtual impactor 1. The virtual impactor portion 1 functions as, for example, a particle condensing device, depending on the settings of the various portions. The secondary flow, wherein the particles from the virtual impactor portion 1 are condensed, is supplied to the particle detector 2, and the particles in the gas are detected.

Note that the setting for the widths of the first flow path in the virtual impactor 1 (referencing FIG. 3 and FIG. 4) correspond to the settings for the flow path width W1 of the jet nozzle opening of the input gas and the flow path width W2 of the vacuum inlet of the opposing nozzle. Moreover, the setting for the width of the second flow path corresponds to the gap (the separation distance) S between the jet nozzle and the opposing nozzle. The flow rate in the first flow path can be checked by measuring the pressure between the particle detecting portion 2 and the pump portion 3 at the first flow path (that is, the pressure difference from the flow path inlet). Similarly, the flow rate of the second flow path can be checked by measuring the pressure between the virtual impactor 1 and the pump 4 in the second flow path (that is, the pressure difference from the flow path inlet).

The flow path widths, and the like, in the virtual impactor can be adjusted through a feed-forward technique in this way.

Yet Another Further Example

Figure 8:
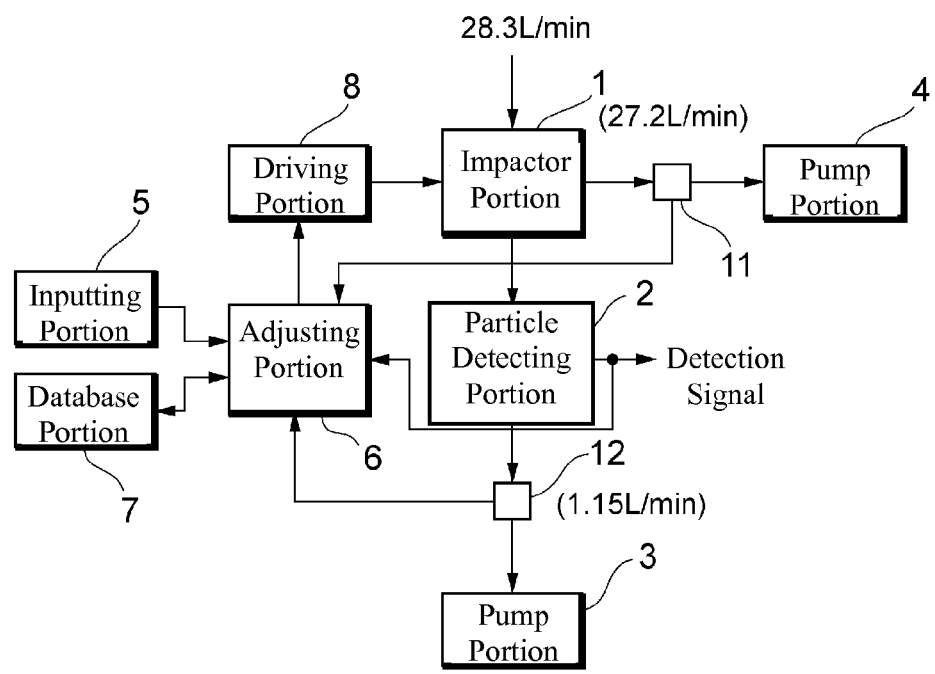
FIG. 8 is an explanatory diagram for explaining an example of feedback control of flow path widths in a variable flow path width virtual impactor according to the present invention.

FIG. 8 is an explanatory diagram for explaining an example of a particle detecting device that is provided with a variable flow path width virtual impactor. In this example, the flow path widths of the virtual impactor are adjusted to predetermined values (target values) using a so-called feedback technique. In FIG. 8, parts corresponding to FIG. 7 are assigned identical codes, and explanations of these parts are omitted.

In the present example, the particle detecting device has, in addition to the structure of Another Further Example, that is, in addition to the virtual impactor portion (particle condensing device) 1, the particle detecting portion 2, the air pump 3 (first pump), the air pump 4 (second pump), the inputting portion 5, the controlling portion 6 (the computer system), the database portion 7, the driving portion 8, and the like, is also provided with flow rate/flow pressure detecting instruments (hereinafter termed simply "detectors") 11 and 12. The instruments for detecting the gas flow rates within the flow paths and the pressures of the gas flows (the flow pressures) can use commercially available products.

The detector 11 is inserted in the flow path between the virtual impactor 1 and the pump portion 4 to detect the flow rate and flow pressure of the primary flow that is exhausted from the virtual impactor 1 (where the detector 11 corresponds to the second detecting unit). The detected values for the flow rate value/flow pressure value are sent to the controlling portion 6 as an electric signal (a first detection signal). This makes it possible for the controlling portion 6 to ascertain accurately the current flow rate and flow pressure of the primary flow. The detector 12 is inserted in the flow path between the particle detector 2 and the pump portion 3 to detect the flow rate and flow pressure of the secondary flow that is exhausted from the virtual impactor 1 (where the detector 12 corresponds to the first detecting unit). The detected values for the flow rate value/flow pressure value are sent to the controlling portion 6 as an electric signal (a second detection signal). The controlling portion 6 is able to ascertain accurately the current flow rate and flow pressure of the secondary flow. The particle detector 2 detects the number of particles, and particle diameters, of the particles in the gas of the secondary flow that is exhausted from the virtual impactor 1. The detected values for the particles are sent to the controlling portion 6 as electric signals (third detection signals). The controlling portion 6 is able to ascertain accurately the current number of particles, and the particle diameters, of the particles in the gas of the secondary flow. The controlling portion 6 evaluates whether or not the current number of particles and particle diameters of the particles in the secondary flow are within a range that is set in advance for the gas of the secondary flow, able to evaluate whether or not particles are detected, and so forth. This is used as one indicator for evaluating whether or not the adjustment of the virtual impactor 1 is correct. If not correct, then the virtual impactor 1 is subjected to readjustment. Moreover, a signal can be sent to the outside to attract the attention of an operator, or the like (not shown).

In addition to the function for setting the various mechanisms of the adjusting portion, described above, in response to the input conditions, the controlling portion 6, readjusts the flow path widths W1, W2, and S of the virtual impactor 1, which have already been set, depending on the amount of error in order to satisfy the specific conditions, based on the first and second detection signals. Moreover, if necessary the vacuum flow of each pump portion is adjusted as well. The controlling portion 6 constantly monitors the first through third detection signals, to perform control so as to maintain the operating conditions in the particle detecting device at the target status.

As described above, when a virtual impactor wherein the flow path width is fixed (a fixed flow path width virtual impactor, which is the virtual impactor of the comparative example) is used, and air pump and a regulator are required in order to properly draw the gas at the specific flow rate, but the need for the regulator can be eliminated through the use of a virtual impactor of a variable flow path width structure, as in the present example. Moreover, because the pressure loss of the regulator is eliminated, the vacuum pressure of the pump can be reduced by that much, making it possible to reduce power consumption. Moreover, it is possible to use the conserved electric power or vacuum power in other parts instead.

Moreover, it is possible to vary the selection characteristics of the sizes (masses) of the particles in the virtual impactor by varying the flow path widths W1 and W2, the exhaust flow rate, and the like, in the secondary flow of the virtual impactor. Doing so makes it possible to select (sort) the size of the particles with a single virtual impactor, without using a structure that selects the outputs of multiple virtual impactors.

The use of the variable flow path width virtual impactor of the present example makes it possible to concentrate particles in the gas using the virtual impactor, to perform particle detection.

Moreover, because it is possible to separate the sizes of particles in the gas using different reference values using a single virtual impactor, through the use of the variable flow path width virtual impactor of the present example, this enables structuring the device more cheaply than in the case wherein an output is selected from a plurality of virtual impactors having different reference values.

Extended Examples

While the present invention has been explained above in reference to the examples, the present invention is not limited to the examples set forth above. The structures and details in the present invention may be varied in a variety of ways, as can be understood by one skilled in the art, within the scope of technology in the present invention.

The invention claimed is:

1. A virtual impactor comprising:
   a first flow path in which a fluid that includes particles flows;
   a second flow path that has a intersecting portion that intersects the first flow path, and branches a portion of the fluid; and
   a flow path width adjusting unit that changes a width of a flow path at the intersecting portion between the first flow path and the second flow path, to set a cross-sectional area of the fluid to a desired value, wherein
   the flow path width adjusting unit comprises:
   four flow path structuring members disposed in a form of a matrix;
   a top plate and a bottom plate, holding both faces of the four flow path structuring members therebetween; and
   a distance adjusting unit that sets a separation distance between flow path structuring members.

* * * * *